United States Patent
Hachtel et al.

(10) Patent No.: US 8,586,612 B2
(45) Date of Patent: Nov. 19, 2013

(54) PIPERIDINESULFONYLUREAS AND -THIOUREAS, THEIR PREPARATION, THEIR USE AND PHARMACEUTICAL COMPOSITIONS COMPRISING THEM

(75) Inventors: Stephanie Hachtel, Frankfurt (DE); Heinrich Christian Englert, Hofheim (DE); Uwe Gerlach, Hattersheim (DE); Heinz Goegelein, Frankfurt (DE); Holger Heitsch, Mainz-Kastel (DE); Karl-Heinz Lehr, Frankfurt (DE); Stefania Pfeiffer-Marek, Frankfurt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 154 days.

(21) Appl. No.: 11/761,565

(22) Filed: Jun. 12, 2007

(65) Prior Publication Data

US 2008/0033016 A1 Feb. 7, 2008

Related U.S. Application Data

(63) Continuation of application No. PCT/EP2005/013087, filed on Dec. 7, 2005.

(30) Foreign Application Priority Data

Dec. 18, 2004 (DE) .......................... 10 2004 061 017

(51) Int. Cl.
*A61K 31/445* (2006.01)

(52) U.S. Cl.
USPC ........................................................ 514/331

(58) Field of Classification Search
None
See application file for complete search history.

(56) References Cited

U.S. PATENT DOCUMENTS

| | | | |
|---|---|---|---|
| 3,829,434 A | 8/1974 | Evanega et al. | |
| 3,887,561 A | 6/1975 | Evanega et al. | |
| 3,914,416 A | 10/1975 | Gueyne et al. | |
| 3,936,455 A | 2/1976 | Wiedermann | |
| 3,944,524 A | 3/1976 | Evanega et al. | |
| 3,987,172 A | 10/1976 | Evanega et al. | |
| 4,315,940 A | 2/1982 | Hitzel et al. | |
| 5,260,318 A | 11/1993 | Lubisch et al. | |
| 5,476,850 A | 12/1995 | Englert | |
| 5,574,843 A | 11/1996 | Gerlach | |
| 5,652,268 A | 7/1997 | Englert | |
| 5,698,596 A | 12/1997 | Englert et al. | |
| 5,792,788 A | 8/1998 | Englert | |
| 5,849,755 A | 12/1998 | Englert | |
| 6,410,573 B1 | 6/2002 | Heitsch | |
| 6,414,030 B1 | 7/2002 | Wirth | |
| 2002/0082300 A1 * | 6/2002 | Wirth et al. | 514/584 |

OTHER PUBLICATIONS

Wermuth CG. Molecular variations based on isoteric replacements. (The Practice of Medicinal Chemistry, 203-237, 1996).*
Sarges et al. Sulfamylurea hypoglycemic agents. (J Med Chem 19(5):695-709, 1976).*
Williams et al (Foye's Principles of Medicinal Chemistry, 5th Edition, pp. 59-63, 2002).*
Brady, et al., Some Aminoethylpiperidines and -pyridines, J. Org. Chem. 26; 1961; pp. 4757-4758.
Gogelein, et al., HMR 1883, a Novel Cardioselective Inhibitor of the ATP-Sensitive Potassium Channel., J. Pharmacol. Exp. Ther. 286: 1998; pp. 1453-1464.
Inagaki, et al., A Family of Sulfonylurea Receptors Determines the Pharmacological Properties of ATP-Sensitive K+ Channels, Neuron, 16; 1996; pp. 1011-1017.
Inagaki, et al., Reconstitution of I(KATP): An Inward Rectifier Subunit Plus the Sulfonylurea Receptor, Science, 270; 1995; pp. 1166-1170.
Mayer, et al., Structural Factors Affecting the Basicity of w-Pyridylalkanols, w-Pyridylalkanamides and w-Pyridylalkylamines., Helv. Chim. Acta, 65; 1982; pp. 1868-1884.
Sarges, et al., SUlfamylurea Hypoglycemic Agents., J. Med. Chem.. 19; 1976; pp. 695-709.
Yoneda, et al., Synthesis of Polyamine Derivatives Having Non-hypotensive Ca2+-Permeable AMPA Receptor Antagonist Activity, Bioorg. Med. Chem. Lett., 11; 2001; pp. 1261-1264.

* cited by examiner

*Primary Examiner* — Craig Ricci
(74) *Attorney, Agent, or Firm* — Scully, Scott, Murphy & Presser, P.C.

(57) ABSTRACT

The present invention relates to piperidinesulfonylureas and piperidinesulfonylthioureas of formula I,

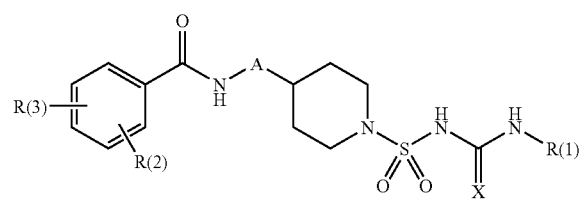

in which A, X, R(1), R(2) and R(3) have the meanings indicated in the claims. The compounds of formula I are valuable active pharmaceutical ingredients which show in particular an inhibiting effect on ATP-sensitive potassium channels of the cardiac muscle and are suitable, for example, for the treatment of disorders of the cardiovascular system such as coronary heart disease, arrhythmias, cardiac insufficiency, cardiomyopathies or reduced contractility of the heart or for the prevention of sudden cardiac death. The invention further relates to processes for preparing the compounds of formula I, their use and pharmaceutical compositions comprising them.

7 Claims, No Drawings

PIPERIDINESULFONYLUREAS AND -THIOUREAS, THEIR PREPARATION, THEIR USE AND PHARMACEUTICAL COMPOSITIONS COMPRISING THEM

The present invention relates to piperidinesulfonylureas and piperidinesulfonylthioureas of the formula I,

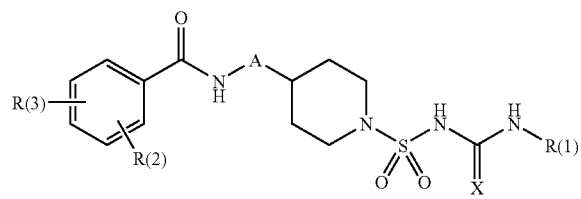

in which A, X, R(1), R(2) and R(3) have the meanings indicated below. The compounds of the formula I are valuable active pharmaceutical ingredients which show in particular an inhibiting effect on ATP-sensitive potassium channels of the cardiac muscle and are suitable, for example, for the treatment of disorders of the cardiovascular system such as coronary heart disease, arrhythmias, cardiac insufficiency, cardiomyopathies or reduced contractility of the heart or for the prevention of sudden cardiac death. The invention further relates to processes for preparing the compounds of the formula I, their use and pharmaceutical compositions comprising them.

For certain benzenesulfonylureas, a blood sugar-lowering effect or hypoglycemic effect has been described. Glibenclamide is regarded as the prototype of such blood sugar-lowering sulfonylureas and is used therapeutically as agent for the treatment of diabetes mellitus. Glibenclamide blocks ATP-sensitive potassium channels (KATP channels) and is used in research as a tool for studying such potassium channels. Besides its blood sugar-lowering effect, glibenclamide also has other effects which, however, have not been therapeutically utilizable to date, including an antifibrillatory effect on the heart. However, in the treatment of arrhythmias or of ventricular fibrillation or its pre-stages with glibenclamide the pronounced lowering of blood sugar, which is simultaneously caused by this substance, would in many cases be undesired or even dangerous because it may further worsen the patient's condition, so that glibenclamide is not generally suitable as an antiarrhythmic clinically.

Various publications, for example U.S. Pat. No. 5,574,069, U.S. Pat. No. 5,698,596, U.S. Pat. No. 5,476,850, U.S. Pat. No. 5,652,268, U.S. Pat. No. 6,410,573 or Gögelein et al., J. Pharmacol. Exp. Ther. 286, 1453-1464 (1998), disclose antifibrillatory benzenesulfonylureas and -thioureas which selectively block myocardial KATP channels (SUR2A/Kir6.2 isoform) and have only a slight hypoglycemic effect. U.S. Pat. No. 6,414,030 describes the effect of some of these compounds on the autonomic nervous system. However, there is still a need for compounds which have an improved profile of pharmacodynamic and pharmacokinetic properties and which are suitable in particular for the treatment of a disturbed cardiac rhythm and its sequelae such as sudden cardiac death or a weakened myocardial contractile force, especially in ischemic conditions.

Certain compounds of the formula I in which X is oxygen, and structurally related compounds have been disclosed. For example, in U.S. Pat. No. 3,829,434, U.S. Pat. No. 3,887,561, U.S. Pat. No. 3,914,426, U.S. Pat. No. 3,936,455 or U.S. Pat. No. 4,315,9404-acylaminoethylpiperidine-1-sulfonylureas have been described which comprise in the acyl group, instead of the benzene ring depicted in formula I, a heterocyclic ring such as, for example, pyridine, quinoline, tetrahydrodioxopyrimidine or oxoisoindoline and which have a hypoglycemic effect and are suitable for the treatment of diabetes mellitus. Sarges et al., J. Med. Chem. 19, 695-709 (1976), describe further piperidinesulfonylureas which are structurally related to the compounds of the formula I and have hypoglycemic effects, and the compounds of the formula I in which A is $CH_2$ or $CH_2$—$CH_2$, X is oxygen, R(1) is n-propyl, n-hexyl or cyclohexyl, and the phenyl group carrying the groups R(2) and R(3) is 5-chloro-2-methoxyphenyl. There are no indications therein that the described compounds have any further pharmacological effects. Surprisingly it has now been found that the piperidinesulfonylureas and -thioureas of the formula I show an inhibiting effect on ATP-sensitive potassium channels in the heart and have a favorable profile of properties, for example as regards their selectivity, and are suitable for the treatment of disorders of the cardiovascular system such as, for example, arrhythmias and for the prevention of sudden cardiac death.

Accordingly, the present invention relates to compounds of the formula I,

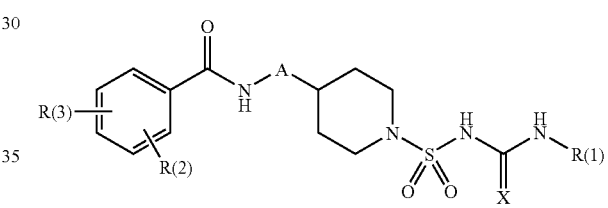

in which
A is $CH_2$, $CH_2$—$CH_2$ or $CH_2$—$CH_2$—$CH_2$;
X is oxygen or sulfur;
R(1) is hydrogen, $(C_1-C_6)$-alkyl, $(C_3-C_7)$-cycloalkyl or —$(C_1-C_3)$-alkyl-$(C_3-C_7)$-cycloalkyl, where the $(C_3-C_7)$-cycloalkyl groups can be substituted one or more times by $(C_1-C_4)$-alkyl, and the $(C_1-C_6)$-alkyl, $(C_3-C_7)$-cycloalkyl and —$(C_1-C_3)$-alkyl-$(C_3-C_7)$-cycloalkyl groups can be substituted one or more times by fluorine;
R(2) and R(3), which are independent of one another and can be identical or different, are hydrogen, halogen, $(C_1-C_4)$-alkyl or $(C_1-C_4)$-alkoxy, where the $(C_1-C_4)$-alkyl and $(C_1-C_4)$-alkoxy groups can be substituted one or more times by fluorine;
in all their stereoisomeric forms and mixtures thereof in all ratios, and their physiologically acceptable salts,
where R(1) cannot be n-propyl, n-hexyl or cyclohexyl if at the same time A is $CH_2$ or $CH_2$—$CH_2$, X is oxygen and the phenyl group carrying the groups R(2) and R(3) is 5-chloro-2-methoxyphenyl.

When groups or substituents can occur more than once in the compounds of the formula I, they can all independently of one another have the indicated meanings and can in each case be identical or different.

Alkyl denotes straight-chain and branched saturated hydrocarbon residues. This also applies when the alkyl group is substituted or is present in another group, for example in an alkoxy group. Examples of alkyl are methyl, ethyl, n-propyl, isopropyl, n-butyl, sec-butyl, isobutyl, tert-butyl, n-pentyl, 1-methylbutyl, isopentyl, neopentyl, tert-pentyl, n-hexyl and isohexyl. Examples of alkoxy are methoxy, ethoxy, n-propoxy, isopropoxy, n-butoxy, isobutoxy, sec-butoxy and tert-butoxy. If an alkyl group or alkoxy group is substituted one or more times by fluorine, it can be substituted by 1, 2, 3, 4, 5, 6, 7, 8, 9, 10, 11, 12 or 13 fluorine atoms. The fluorine atoms can be present at any positions in the alkyl group or the alkoxy group. Examples of fluorine-substituted alkyl groups are trifluoromethyl, 2-fluoroethyl, 2,2,2-trifluoroethyl, pentafluoroethyl, 3,3,3-trifluoropropyl, 2,2,3,3,3-pentafluoropropyl and heptafluoroisopropyl. Examples of fluorine-substituted alkoxy groups are trifluoromethoxy, 2,2,2-trifluoroethoxy, pentafluoroethoxy and 3,3,3-trifluoropropoxy.

Examples of cycloalkyl are cyclopropyl, cyclobutyl, cyclopentyl, cyclohexyl and cycloheptyl. If a cycloalkyl group is substituted one or more times by alkyl groups, it can be substituted, for example, by 1, 2, 3 or 4 identical or different alkyl groups. Examples of alkyl substituents on a cycloalkyl group are methyl, ethyl, isopropyl and tert-butyl, in particular methyl. Alkyl substituents can be present at any positions in the cycloalkyl group, for example at the 1 position, i.e. on the carbon atom by which the cycloalkyl group is bonded, the 2 position, the 3 position or the 4 position. Examples of alkyl-substituted cycloalkyl groups are 1-methylcyclopropyl, 2,2-dimethylcyclopropyl, 1-methyl cyclopentyl, 2,3-dimethylcyclopentyl, 4-methylcyclohexyl, 4-tert-butylcyclohexyl and 3,3,5,5-tetramethylcyclohexyl. If a cycloalkyl group is substituted one or more times by fluorine, it can be substituted by 1, 2, 3, 4, 5, 6, 7, 8, 9, 10, 11, 12 or 13 fluorine atoms, for example. A cycloalkyl group can also be substituted simultaneously by fluorine and alkyl. The fluorine atoms can be present at any positions in the cycloalkyl group and can also be present in an alkyl substituent on the cycloalkyl group. Examples of fluorine-substituted cycloalkyl groups are 1-fluorocyclohexyl, 4,4-difluorocyclohexyl and 3,3,4,4,5,5-hexafluorocyclohexyl.

The above explanations accordingly apply to the alkyl subgroup and the cycloalkyl subgroup in the —($C_1$-$C_3$)-alkyl-($C_3$-$C_7$)-cycloalkyl group which is bonded via the ($C_1$-$C_3$)-alkyl group to the remainder of the molecule. A —($C_1$-$C_3$)-alkyl-($C_3$-$C_7$)-cycloalkyl group can be substituted by fluorine in the alkyl subgroup and/or in the cycloalkyl subgroup, and/or be substituted by alkyl in the cycloalkyl subgroup. Examples of —($C_1$-$C_3$)-alkyl-($C_3$-$C_7$)-cycloalkyl are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-, 2-cyclopropyl-1-methylethyl-, 2-cyclobutyl-1-methylethyl-, 2-cyclopentyl-1-methylethyl-, 2-cyclohexyl-1-methylethyl-, 2-cycloheptyl-1-methylethyl-, 3-cyclopropylpropyl-, 3-cyclopentylpropyl-, 3-cyclohexylpropyl-, and 3-cycloheptylpropyl-.

Halogen denotes fluorine, chlorine, bromine or iodine, preferably chlorine or fluorine.

The groups R(2) and R(3) can be present at any positions on the phenyl group carrying them. The carbon atoms not carrying the groups R(2) and R(3) and the CO group in the phenyl group depicted in formula I carry hydrogen atoms. It is thus possible in substituted phenyl groups for the substituents to be present at any positions. In monosubstituted phenyl groups, the substituent can be present at the 2 position, the 3 position or the 4 position. In disubstituted phenyl groups, the substituents can be present at the 2,3 position, 2,4 position, 2,5 position, 2,6 position, 3,4 position or 3,5 position. Examples of the phenyl group carrying the groups R(2) and R(3) are unsubstituted phenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-isobutylphenyl, 3-isobutylphenyl, 4-isobutylphenyl, 2-tert-butylphenyl, 3-tert-butylphenyl, 4-tert-butylphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2-isobutoxyphenyl, 3-isobutoxyphenyl, 4-isobutoxyphenyl, 2-tert-butoxyphenyl, 3-tert-butoxyphenyl, 4-tert-butoxyphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-trifluoromethylphenyl, 3-trifluoromethylphenyl, 4-trifluoromethylphenyl, 3,4-bis(trifluoromethyl)phenyl, 3,5-bis(trifluoromethyl)phenyl, 2-trifluoromethoxyphenyl, 3-trifluoromethoxyphenyl, 4-trifluoromethoxyphenyl, etc., and, in the case of substituted phenyl groups carrying two different substituents from the substituents embraced by the definition of R(2) and R(3), all possible combinations with respect to the kind of the substituents and with respect to their positions on the phenyl ring including for example, in the case of a phenyl group substituted by fluorine and methyl, 3-fluoro-2-methylphenyl, 4-fluoro-2-methylphenyl, 5-fluoro-2-methylphenyl, 2-fluoro-6-methylphenyl, 2-fluoro-3-methylphenyl, 4-fluoro-3-methylphenyl, 3-fluoro-5-methylphenyl, 2-fluoro-5-methylphenyl, 2-fluoro-4-methylphenyl, 3-fluoro-4-methylphenyl, in the case of a phenyl group substituted by fluorine and methoxy, 3-fluoro-2-methoxyphenyl, 4-fluoro-2-methoxyphenyl, 5-fluoro-2-methoxyphenyl, 2-fluoro-6-methoxyphenyl, 2-fluoro-3-methoxyphenyl, 4-fluoro-3-methoxyphenyl, 3-fluoro-5-methoxyphenyl, 2-fluoro-5-methoxyphenyl, 2-fluoro-4-methoxyphenyl, 3-fluoro-4-methoxyphenyl, in the case of a phenyl group substituted by chlorine and methoxy, 3-chloro-2-methoxyphenyl, 4-chloro-2-methoxyphenyl, 5-chloro-2-methoxyphenyl, 2-chloro-6-methoxyphenyl, 2-chloro-3-methoxyphenyl, 4-chloro-3-methoxyphenyl, 3-chloro-5-methoxyphenyl, 2-chloro-5-methoxyphenyl, 2-chloro-4-methoxyphenyl, 3-chloro-4-methoxyphenyl, in the case of phenyl group substituted by chlorine and trifluoromethoxy, 3-chloro-2-trifluoromethoxyphenyl, 4-chloro-2-trifluoromethoxyphenyl, 5-chloro-2-trifluoromethoxyphenyl, 2-chloro-6-trifluoromethoxyphenyl, 2-chloro-3-trifluoromethoxyphenyl, 4-chloro-3-trifluoromethoxyphenyl, 3-chloro-5-trifluoromethoxyphenyl, 2-chloro-5-trifluoromethoxyphenyl, 2-chloro-4-trifluoromethoxyphenyl, 3-chloro-4-trifluoromethoxyphenyl, in the case of a phenyl group substituted by tert-butyl- and methoxy, 3-tert-butyl-2-methoxyphenyl, 4-tert-butyl-2-methoxyphenyl, 5-tert-butyl-2-methoxyphenyl, 2-tert-butyl-6-methoxyphenyl, 2-tert-butyl-3-methoxyphenyl, 4-tert-butyl-3-methoxyphenyl, 3-tert-butyl-5-methoxyphenyl, 2-tert-butyl-5-methoxyphenyl, 2-tert-butyl-4-methoxyphenyl, 3-tert-butyl-4-methoxyphenyl, etc.

The present invention includes all stereoisomeric forms of the compounds of the formula I, for example all possible enantiomers and diastereomers. Centers of asymmetry which are present in the compounds of the formula I, for example in the groups R(1), R(2), R(3), can all independently of one another have the S configuration or the R configuration. The invention likewise includes mixtures of two or more stereoisomeric forms, for example mixtures of enantiomers and/or diastereomers, in all ratios. For example, the invention includes enantiomers in enantiomerically pure and in substantially enantiomerically pure form, both as levorotatory and as dextrorotatory antipodes, in the form of racemates, and in the form of mixtures of the two enantiomers in all ratios. The invention includes diastereomers in the form of pure and substantially pure diastereomers, including meso compounds, for example, and in the form of mixtures of two or more diastereomers in all ratios. If a cis/trans isomerism (or E/Z isomerism) is present, the invention includes the cis form, the trans form and mixtures of these forms in all ratios. Individual stereoisomers can be prepared if desired by separating a mixture by conventional methods, for example by chromatography or crystallization, or by using stereochemically uniform starting substances in the synthesis, or by means of stereoselective reactions. A separation of stereoisomers can be preceded where appropriate by a derivatization. Separation of a stereoisomer mixture can take place at the stage of the compounds of the formula I or at the stage of an intermediate during the synthesis. The invention also includes all tautomeric forms of the compounds of the formula I.

Physiologically acceptable salts of the compounds of the formula I are in particular salts with a non-toxic salt component and preferably pharmaceutically usable salts. They can contain inorganic or organic or salt components. Such salts can be prepared, for example, from compounds of the formula I and non-toxic inorganic or organic bases. Examples of suitable bases are suitable alkali metal compounds or alkaline earth metal compounds, such as sodium hydroxide or potassium hydroxide, or ammonia or organic amino compounds or quaternary ammonium hydroxides. Reactions of compounds of the formula I with bases to prepare the salts are generally carried out by conventional procedures in a solvent or diluent. If acidic groups are present, in many cases the sodium, potassium, magnesium or calcium salts or ammonium salts, which can also carry one or more organic residues on the nitrogen atom, are advantageous salts because of the physiological and chemical stability. Salt formation on the carbamoyl-substituted nitrogen atom of the sulfonamide group leads to compounds of the formula II,

II in which A, X, R(1), R(2) and R(3) have the meanings indicated above, and the cation M is, for example, an alkali metal ion or an equivalent of an alkaline earth metal ion, for example the sodium, potassium, magnesium or calcium ion, or the unsubstituted ammonium ion or an ammonium ion having one or more organic residues. An ammonium ion representing M can also be, for example, the cation obtained from an amino acid, in particular a basic amino acid such as, for example, lysine or arginine, by protonation.

The present invention also includes all salts of the compounds of the formula I which, because of low physiological tolerability, are not directly suitable for use in medicaments but are suitable, for example, as intermediates for chemical reactions or for preparing physiologically acceptable salts, for example by anion exchange or cation exchange. The present invention further includes all solvates of compounds of the formula I, for example hydrates or adducts with alcohols, and derivatives of the compounds of the formula I and prodrugs and active metabolites of compounds of the formula I.

The group A is preferably $CH_2$—$CH_2$.

One embodiment of the present invention relates to compounds of the formula I in which X is sulfur, i.e. compounds of the formula Ia, Ia

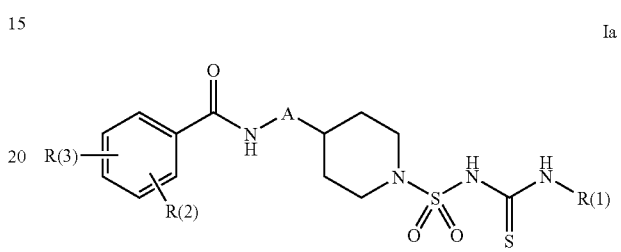

in all their stereoisomeric forms and mixtures thereof in all ratios, and their physiologically acceptable salts. Another embodiment of the invention relates to compounds of the formula I in which X is oxygen, i.e. compounds of the formula Ib, Ib in all their stereoisomeric forms and mixtures thereof in all ratios, and their physiologically acceptable salts. The residues A, R(1), R(2) and R(3) in the formulae Ia and Ib have the meanings indicated above.

R(1) is preferably $(C_1-C_6)$-alkyl, $(C_3-C_7)$-cycloalkyl or —$(C_1-C_3)$-alkyl-$(C_3-C_7)$-cycloalkyl, where the $(C_3-C_7)$-cycloalkyl groups can be substituted one or more times by $(C_1-C_4)$-alkyl, and the $(C_1-C_6)$-alkyl, $(C_3-C_7)$-cycloalkyl and —$(C_1-C_3)$-alkyl-$(C_3-C_7)$-cycloalkyl groups can be substituted one or more times by fluorine. R(1) is particularly preferably $(C_1-C_4)$-alkyl, $(C_3-C_6)$-cycloalkyl or —$CH_2$—$(C_3-C_6)$-cycloalkyl, where the $(C_3-C_6)$-cycloalkyl groups can be substituted once or twice by $(C_1-C_4)$-alkyl, and the $(C_1-C_4)$-alkyl, $(C_3-C_6)$-cycloalkyl and —$CH_2$—$(C_3-C_6)$-cycloalkyl groups can be substituted one or more times by fluorine. R(1) is very particularly preferably $(C_1-C_4)$-alkyl or $(C_3-C_6)$-cycloalkyl, where the $(C_3-C_6)$-cycloalkyl group can be substituted once or twice by $(C_1-C_4)$-alkyl, and the $(C_1-C_4)$-alkyl and $(C_3-C_6)$-cycloalkyl groups can be substituted one or more times by fluorine. R(1) is especially preferably $(C_1-C_3)$-alkyl or cyclopropyl, very especially preferably $(C_1-C_3)$-alkyl, in particular $(C_1-C_2)$-alkyl, all of which can be substituted one or more times by fluorine. The number of carbon atoms in the R(1) group is preferably 1, 2, 3, 4, 5, 6 or 7, particularly preferably 1, 2, 3, 4, 5 or 6, very particularly preferably 1, 2, 3 or 4. The number of carbon atoms in the R(1) group is especially preferably 1, 2 or 3, i.e., in this embodiment of the invention R(1) is methyl, ethyl, n-propyl, isopropyl or cyclopropyl, all of which can also be substituted one or more times by fluorine. In the particular case of compounds of the formula I in which X is oxygen, the number of carbon atoms in the R(1) group is more preferably 1 or 2, i.e., in this embodiment R(1) is methyl or ethyl, both of which can also be substituted one or more times by fluorine. In one embodiment of the present invention, the R(1) group is not substituted by fluorine.

The phenyl group carrying the groups R(2) and R(3) is preferably a substituted phenyl group, i.e., at least one of the group R(2) and R(3) is preferably different from hydrogen. One embodiment relates to compounds of the formula I in which the two groups R(2) and R(3), which can be present at any positions, are different from hydrogen. In this embodiment, one of the groups R(2) and R(3) is preferably at the 2 position and the other is at the 5 position. It is particularly preferred in this embodiment for one $(C_1-C_4)$-alkyl or $(C_1-C_4)$-alkoxy substituent, very particularly preferably one $(C_1-C_4)$-alkoxy substituent, all of which can also be substituted by one or more fluorine atoms, to be at the 2 position, and one $(C_1-C_4)$-alkyl substituent, which can also be substituted by one or more fluorine atoms, or one halogen substituent, very particularly preferably one halogen substituent, to be at the 5 position of the phenyl group. Examples of this embodiment are compounds of the formula I in which the phenyl group carrying the groups R(2) and R(3) is a 2-$(C_1-C_4)$-alkoxy-5-$(C_1-C_4)$-alkylphenyl group or a 2-$(C_1-C_4)$-alkoxy-5-halophenyl group, in particular a 2-$(C_1-C_4)$-alkoxy-5-halophenyl group, for example a 5-chloro-2-methoxyphenyl group, a 5-fluoro-2-methoxyphenyl group or a 5-tert-butyl-2-methoxyphenyl group, where the alkyl groups and alkoxy groups in all these groups can also be substituted by one or more fluorine atoms. In one embodiment of the present invention, alkyl and alkoxy groups representing the two groups R(2) and R(3) are not substituted by fluorine. In another embodiment of the invention, in one of the groups R(2) and R(3) an alkyl or alkoxy group representing this group can be substituted by one or more fluorine atoms. A $(C_1-C_4)$-alkoxy group representing R(2) and/or R(3) is preferably a $(C_1-C_3)$-alkoxy group.

Preferred compounds of the formula I are those compounds in which in the general definition of the compounds of the invention or in a particular embodiment one or more of the groups present therein have preferred meanings, where all combinations of two or more preferred meanings and/or features of particular embodiments are a subject of the present invention. Also with respect to all preferred compounds of the formula I, as well as with respect to all disclosed specific compounds of the formula I, such as, for example, the compounds of the examples, the present invention includes all their stereoisomeric forms and mixtures thereof in all ratios, and all their physiologically acceptable salts.

Thus, for example, a group of preferred compounds of the formula I is formed by those compounds in which X is sulfur and, at the same time, R(1) is $(C_1-C_3)$-alkyl or cyclopropyl, preferably $(C_1-C_3)$-alkyl, or X is oxygen and, at the same time, R(1) is $(C_1-C_2)$-alkyl, where the group A in these compounds is preferably $CH_2-CH_2$ and/or the phenyl group carrying the groups R(2) and R(3) is preferably a 2-$(C_1-C_4)$-alkoxy-5-halophenyl group, particularly preferably a 2-$(C_1-C_3)$-alkoxy-5-halophenyl group, in all their stereoisomeric forms and mixtures thereof in all ratios, and their physiologically acceptable salts. A particularly preferred group of compounds of the formula I is formed by those compounds in which X is sulfur and, at the same time, R(1) is $(C_1-C_3)$-alkyl, or X is oxygen and, at the same time, R(1) is $(C_1-C_2)$-alkyl, and the phenyl group carrying the groups R(2) and R(3) is 5-chloro-2-methoxyphenyl, where the group A in these compounds is preferably $CH_2-CH_2$, in all their stereoisomeric forms and mixtures thereof in all ratios, and their physiologically acceptable salts.

The present invention also relates to processes for preparing the compounds of the formula I which are explained in detail below and by which the compounds according to the invention are obtainable.

Compounds of the formula I in which X is sulfur and R(1) is different from hydrogen, i.e. piperidinesulfonylthioureas of the formula Ia,

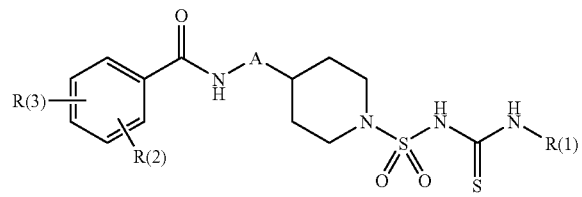

in which A, R(2) and R(3) have the meanings indicated above, and R(1) has the meanings indicated above with the exception of hydrogen, can be prepared, for example, by reacting piperidinesulfonamides of the formula III,

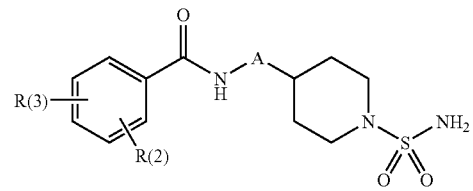

in which A, R(2) and R(3) have the meanings indicated above, in an inert solvent or diluent with a base and with an R(1)-substituted isothiocyanate of the formula IV,

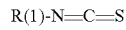

R(1)-N=C=S    IV in which R(1) has the meanings indicated above with the exception of hydrogen. The compounds of the formula IV are commercially available or can be prepared by or in analogy to methods described in the literature from amines of the formula R(1)-$NH_2$, in which R(1) has the meanings indicated above with the exception of hydrogen. Examples of suitable bases are alkali metal and alkaline earth metal hydroxides, hydrides, carbonates, amides and alkoxides, such as sodium hydroxide, potassium hydroxide, calcium hydroxide, sodium hydride, potassium hydride, calcium hydride, potassium carbonate, cesium carbonate, sodium amide, potassium amide, sodium methoxide, sodium ethoxide, potassium tert-butoxide, tertiary amines and quaternary ammonium hydroxides. The reaction of the compound of the formula III with the base can initially be carried out in a separate step, and the resulting salt of formula V,

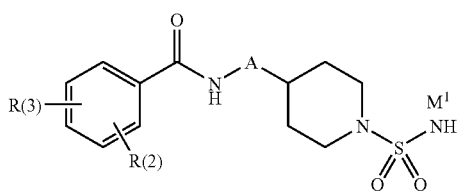

in which A, R(2) and R(3) have the meanings indicated above, and the cation $M^1$ is an alkali metal ion, for example a sodium ion, potassium ion or cesium ion, or an equivalent of an alkaline earth metal ion, for example of a magnesium ion or calcium ion, or is an ammonium ion which is inert under the reaction conditions, for example a quaternary ammonium ion, can also be isolated as intermediate, if desired. However, in a particularly advantageous manner, the salt of the formula V can also be generated in situ from the compound of the formula III and directly reacted with the isothiocyanate of the formula IV. Examples of suitable inert solvents or diluents are ethers such as tetrahydrofuran (THF), dioxane, ethylene glycol dimethyl ether (DME) or diglyme, ketones such as acetone or butanone, nitriles such as acetonitrile, nitro compounds such as nitromethane, esters such as ethyl acetate, amides such as dimethylformamide (DMF) or N-methyl-2-pyrrolidone (NMP), hexamethylphosphoric triamide (HMPT), sulfoxides such as dimethyl sulfoxide (DMSO) or hydrocarbons such as benzene, toluene or xylenes, or mixtures of these solvents. The reaction of the compound of the formula III or V with the compound of the formula IV is generally carried out at temperatures of about 20° C. to about 140° C., in particular of about 40° C. to about 120° C.

Compounds of the formula I in which X is oxygen and R(1) is different from hydrogen, i.e. piperidinesulfonylureas of the formula Ib,

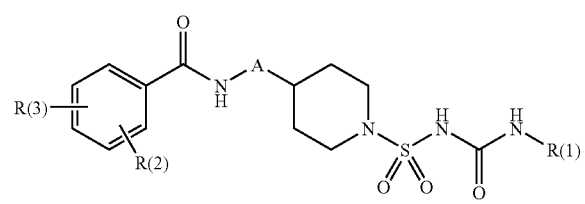

in which A, R(2) and R(3) have the meanings indicated above, and R(1) has the meanings indicated above with the exception of hydrogen, can be prepared, for example, in analogy to the synthesis of the thiourea derivatives of the formula Ia which is described above, by reacting piperidinesulfonamides of the formula III or their salts of the formula V in an inert solvent or diluent with an R(1)-substituted isocyanate of the formula VI, $$R(1)\text{-}N\!\!=\!\!C\!\!=\!\!O \qquad\qquad VI$$

in which R(1) has the meanings indicated above with the exception of hydrogen, and, where appropriate, a base. The above explanations regarding the reaction with isothiocyanates apply correspondingly to the reaction with isocyanates.

Compounds of the formula I in which R(1) is hydrogen can be obtained according to the above-described syntheses by reacting compounds of the formula III or their salts of the formula V, instead of with an isothiocyanate of the formula IV or an isocyanate of the formula VI, with a silyl isothiocyanate or a silyl isocyanate, for example a tri((C$_1$-C$_4$)-alkyl)silyl isothiocyanate or a tri((C$_1$-C$_4$)-alkyl)silyl isocyanate such as trimethylsilyl isothiocyanate or trimethylsilyl isocyanate, which are commercially available, and converting the initially obtained (thio)ureas which are silyl-substituted on the terminal nitrogen atom of the (thio)urea group, by hydrolysis or treatment with a fluoride into the compounds of the formula I in which R(1) is hydrogen.

Piperidinesulfonylureas of the formula Ib in which R(1) is different from hydrogen can also be prepared from piperidinesulfonamides of the formula III or their salts of the formula V by reaction with N—R(1)-substituted 2,2,2-trichloroacetamides of the formula VII, $$Cl_3C\text{—}CO\text{—}NH\text{—}R(1) \qquad\qquad VII$$

in which R(1) has the meanings indicated above with the exception of hydrogen and which are commercially available or can be prepared by or in analogy to methods in the literature from amines of the formula R(1)-NH$_2$, in which R(1) has the meanings indicated above with the exception of hydrogen, and, where appropriate, a base in an inert solvent. The above explanations regarding the reaction with isothiocyanates apply correspondingly also to the reaction with 2,2,2-trichloroacetamides, the latter reaction generally being carried out at elevated temperature, for example at temperatures of approximately 60° C. to approximately 120° C., and preferably using a higher-boiling solvent whose boiling point is at or above the reaction temperature, for example N-methyl-2-pyrrolidone.

The compounds of the formula I can also be prepared by reacting piperidinesulfonyl isothiocyanates and isocyanates of the formula VIII,

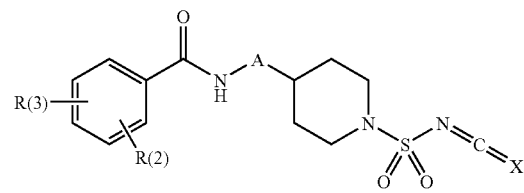

in which A, X, R(2) and R(3) have the meanings indicated above, with amines of the formula R(1)-NH$_2$ in which R(1) has the meanings indicated above. The sulfonyl isocyanates of the formula VIII, in which X is oxygen, can be prepared from the piperidinesulfonamides of the formula III or their salts of the formula V by conventional methods, for example by reaction in an inert solvent with phosgene, N,N'-carbonyldiimidazole or a chloroformic ester, for example a (C$_1$-C$_4$)-alkyl chloroformate such as ethyl chloroformate. Depending on how the reaction is carried out, other intermediates may also occur instead of the isocyanate or in addition to the isocyanate of the formula VIII, for example sulfonylurethanes. To prepare the sulfonyl isothiocyanates of the formula VIII, in which X is sulfur, the piperidinesulfonamides of the formula III or their salts of the formula V can be reacted, for example, with alkali metal hydroxides and carbon disulfide in an inert solvent such as DMF, DMSO or NMP. The obtained dialkali metal salt of the sulfonyldithiocarbamic acid can be reacted in an inert solvent with phosgene or a phosgene substitute such as triphosgene or with a chloroformic ester or with thionyl chloride. The sulfonyl isocyanate or isothiocyanate of the formula VIII or other intermediate, which is generally obtained in the form of a solution, can then be reacted in situ with an amine of the formula R(1)-NH$_2$ in which R(1) has the meanings indicated above including, specifically for the preparation of compounds of the formula I in which R(1) is hydrogen, ammonia.

Piperidinesulfonylureas of the formula Ib can also be prepared from the corresponding piperidinesulfonylthioureas of the formula Ia by a desulfurization, i.e. conversion of the C=S group into the C=O group. Replacement of the sulfur atom in the C=S group of the compounds of the formula Ia by an oxygen atom can be achieved, for example, by treating the compound of the formula Ia with an oxide or salt of a heavy metal or with an oxidizing agent in an inert solvent or diluent, for example water or a mixture of water and an organic solvent. Examples of suitable oxidizing agents for the desulfurization are peroxides such as hydrogen peroxide or sodium peroxide, or nitrous acid.

The intermediates of the formula III, i.e. the corresponding 4-(benzamidomethyl)piperidine-1-sulfonamides, 4-(2-benzamidoethyl)piperidine-1-sulfonamides and 4-(3-benzamidopropyl)piperidine-1-sulfonamides, can be prepared by or in analogy to methods in the literature as described, for example, in Sarges et al., J. Med. Chem. 19, 695-709 (1976). For this purpose, the 4-aminomethylpiperidine-1-sulfonamide or the 4-(2-aminoethyl)piperidine-1-sulfonamide or the 4-(3-aminopropyl)piperidine-1-sulfonamide or a salt thereof, for example the hydrochloride, can be acylated under standard conditions with the appropriate benzoic acids or reactive derivatives thereof, for example benzoyl chlorides, benzoic anhydrides or reactive esters. If the acylation is to be carried out with a benzoic acid, generally the acid is initially activated with a conventional coupling reagent, for example propanephosphonic anhydride (PPA), N,N'-carbonyldiimidazole (CDI), a carbodiimide such as N,N'-diisopropylcarbodiimide (DIC), N,N'-dicyclohexylcarbodiimide (DCC) or N-ethyl-N'-(3-dimethylaminopropyl)carbodiimide hydrochloride (EDC), O-(cyano(ethoxycarbonyl)methyleneamino)-N,N,N',N'-tetramethyluronium tetrafluoroborate (TOTU) or ethyl-1,2-dihydro-2-ethoxy-1-quinolinecarboxylate (EEDQ), or, for example, converted into a mixed anhydride with a chloroformic ester such as ethyl or isobutyl chloroformate. The acylation usually takes place in the presence of a suitable base, for example a tertiary amine such as triethylamine or ethyl diisopropylamine or an alkali metal carbonate such as sodium carbonate.

The 4-aminomethylpiperidine-1-sulfonamide, 4-(2-aminoethyl)piperidine-1-sulfonamide and 4-(3-aminopropyl)piperidine-1-sulfonamide or a salt thereof such as, for example, the hydrochloride can be prepared, for example, by the method for preparing 4-(2-aminoethyl)piperidine-1-sulfonamide described in Sarges et al., J. Med. Chem. 19, 695-709 (1976), by converting 4-phthalimidomethylpiperidine or 4-(2-phthalimidoethyl)piperidine or 4-(3-phthalimidopropyl)piperidine or a salt thereof such as, for example, the hydrochloride by reaction with sulfamide $SO_2(NH_2)_2$ in pyridine at the reflux temperature into the 4-phthalimidoalkylpiperidine-1-sulfonamide, and eliminating the phthaloyl group therefrom by treatment with hydrazine in methanol at reflux temperature and subsequently with hydrochloric acid. 4-(2-Phthalimidoethyl)piperidine can be obtained, for example, according to the synthesis described in Sarges et al., J. Med. Chem. 19, 695-709 (1976), by reacting 4-(2-aminoethyl)pyridine, which is described in Brady et al., J. Org. Chem. 26, 4757-4758 (1961), in xylene in the presence of triethylamine with phthalic anhydride, and converting the pyridine ring in the resulting 4-(2-phthalimidoethyl)pyridine by catalytic hydrogenation, for example in the presence of a transition metal catalyst such as platinum dioxide, into the piperidine ring. 4-(Phthalimidomethyl)piperidine, which is described in Yoneda et al., Bioorg. Med. Chem. Lett. 11, 1261-1246 (2001), can be obtained, for example, from commercially available 4-aminomethylpiperidine by reaction with phthalic anhydride, and 4-(3-phthalimidopropyl)piperidine can be obtained in analogy to 4-(2-phthalimidoethyl)piperidine from 4-(3-phthalimidopropyl)pyridine whose synthesis is described in Mayer et al., Helv. Chim Acta 65, 1868-1884 (1982).

The compounds of the formula III can also be synthesized via other reaction sequences. For example, to prepare compounds of the formula III in which A is $CH_2$—$CH_2$, initially 4-(2-aminoethyl)pyridine can be acylated on the primary amino group with the appropriate benzoic acid or a reactive derivative thereof, for example with 5-chloro-2-methoxybenzoyl chloride in the case of the preparation of compounds in which the phenyl group carrying the groups R(2) and R(3) is a 5-chloro-2-methoxyphenyl group. The above explanations apply correspondingly to this acylation. The pyridine ring in the acylation product can then be converted by catalytic hydrogenation, for example in the presence of a transition metal catalyst such as platinum dioxide, into the piperidine ring, with the reaction conditions to be chosen where appropriate so that substituents present in the benzoyl group are not adversely affected, as is explained in Sarges et al., J. Med. Chem. 19, 695-709 (1976), and is familiar to the skilled person. The resulting 4-(2-benzamidoethyl)piperidine can then be converted with sulfamide, for example in DME at the reflux temperature, into the compound of the formula III. Compounds of the formula III in which A is $CH_2$ or $CH_2$—$CH_2$—$CH_2$ can be prepared in an analogous manner by starting from 4-aminomethylpyridine or 4-(3-aminopropyl)pyridine.

The compounds of the formula I inhibit ATP-sensitive potassium channels and influence the action potential of cells, especially of myocardial cells or cardiac muscle cells. They have in particular a normalizing effect on a disturbed action potential as is present, for example, in cases of ischemia, and are suitable, for example, for the treatment of disorders of the cardiovascular system or of heart diseases. The compounds of the formula I are particularly suitable for the treatment of arrhythmias and their sequelae, for example ventricular fibrillation or sudden cardiac death, and for the treatment of a reduced contractility of the heart as may occur as a consequence of coronary heart disease, cardiac insufficiency or cardiomyopathy. Treatment of diseases here includes the therapy of existing pathological changes or dysfunctions of the body or of existing symptoms with the aim of alleviation, diminution or cure, as well as the prophylaxis or prevention of pathological changes or dysfunctions of the body or of symptoms in humans or animals, who are susceptible thereto and require such a prophylaxis or prevention, with the aim of preventing or reducing their occurrence or attenuating them in the event of their occurrence. As an example, a preventive medication with the aim of preventing sudden cardiac death or the occurrence of a myocardial infarction in patients, who are susceptible to myocardial reinfarctions or sudden cardiac death caused by arrhythmias, may be mentioned. The treatment of diseases applies both to acute and to chronic cases.

The activity of the compounds of the formula I can be demonstrated, for example, in the pharmacological model which is described below and in which the action potential duration is determined on the guinea pig papillary muscle. The selectivity of the compounds can be demonstrated in the pharmacological models which are described below and in which the hypoglycemic effect and the effect on coronary flow are determined. Preferred compounds of the formula I act as selective inhibitors of the cardiac ATP-sensitive potassium channel (SUR2A/Kir6.2 isoform). Owing to an only small effect on the pancreatic and the vascular ATP-sensitive potassium channel (SUR1/Kir6.2 and SUR2B/Kir6.2 isoforms), such substances do not lead to a substantial lowering of the blood sugar level, or blood glucose level, which is generally unwanted in non-diabetic patients, nor to a constriction of blood vessels, especially coronary vessels, which would lead to a generally unwanted reduction in blood flow. On the other hand, in diabetic patients an effect on the pancreatic ATP-sensitive potassium channel and the reduction in the blood sugar level which is associated therewith, may be advantageous for the treatment of, for example, cardiac arrhythmias or a reduced contractility of the heart associated with coronary heart disease or for the prevention of sudden cardiac death, and a respective profile of properties of a compound of the formula I may be aimed at. In addition, the compounds of the formula I can also have an effect on the peripheral and/or central autonomic nervous system and, in particular, influence ATP-sensitive potassium channels of the vagal or parasympathetic nervous system. They therefore have a stimulating effect on the vagal nervous system, in particular a stimulating effect on the vagal nervous system of the heart through inhibition of ATP-sensitive potassium channels on the cardiac nerve, and are suitable for the treatment of a vagal dysfunction or of a sympathovagal imbalance, especially a vagal dysfunction of the heart. A dysfunction of the vagal nervous system of the heart can, for example, occur temporarily in the event of a cardiac oxygen deficit which may lead to a reduced secretion of vagal neurotransmitters, for instance acetylcholine.

The compounds of the formula I and their physiologically acceptable salts can therefore be used on animals, preferably on mammals, and in particular on humans, as pharmaceutical or medicament on their own, in mixtures with one another or in the form of pharmaceutical compositions or pharmaceutical products. Examples of mammals on which the compounds of the formula I can be used or tested are monkeys, dogs, mice, rats, rabbits, guinea pigs, cats and larger productive animals such as, for example, cattle and pigs. The present invention also relates to the compounds of the formula I defined as indicated above, and their physiologically acceptable salts for use as pharmaceutical, and pharmaceutical compositions, or pharmaceutical preparations, and pharmaceutical products and medicaments which comprise an effective dose of at least one compound of the formula I as defined above, and/or of a physiologically acceptable salt thereof as active ingredient and a pharmaceutically acceptable carrier, i.e. one or more pharmaceutically acceptable carrier substances and/or auxiliary substances.

The invention also relates to the use of compounds of the formula I,

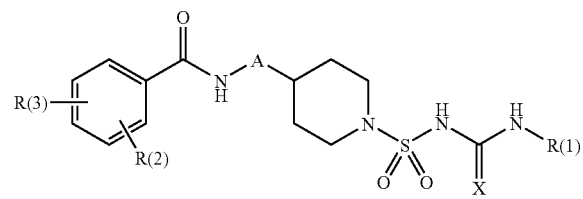

in which
A is $CH_2$, $CH_2$—$CH_2$ or $CH_2$—$CH_2$—$CH_2$;
X is oxygen or sulfur;

R(1) is hydrogen, $(C_1-C_6)$-alkyl, $(C_3-C_7)$-cycloalkyl or —$(C_1-C_3)$-alkyl-$(C_3-C_7)$-cycloalkyl, where the $(C_3-C_7)$-cycloalkyl groups can be substituted one or more times by $(C_1-C_4)$-alkyl, and the $(C_1-C_6)$-alkyl, $(C_3-C_7)$-cycloalkyl and —$(C_1-C_3)$-alkyl-$(C_3-C_7)$-cycloalkyl groups can be substituted one or more times by fluorine;
R(2) and R(3), which are independent of one another and can be identical or different, are hydrogen, halogen, $(C_1-C_4)$-alkyl or $(C_1-C_4)$-alkoxy, where the $(C_1-C_4)$-alkyl and $(C_1-C_4)$-alkoxy groups can be substituted one or more times by fluorine;
in all their stereoisomeric forms and mixtures thereof in all ratios, and their physiologically acceptable salts, for manufacturing a medicament for the treatment of the diseases mentioned above and hereinafter, especially of disorders of the cardiovascular system, heart diseases, arrhythmias, ventricular fibrillation, sudden cardiac death, reduced contractility of the heart, ischemias of the heart, coronary heart disease, angina pectoris, cardiac insufficiency, cardiomyopathy, cardiac hypertrophy or vagal dysfunction of the heart, where the treatment of diseases encompasses, as explained, the therapy and prophylaxis thereof, as well as the use of the compounds defined afore for manufacturing a medicament for inhibiting ATP-sensitive potassium channels in the heart, especially the cardiac muscle or myocardium. The invention also relates to methods for the treatment of the diseases mentioned above and hereinafter, which comprise administering an effective amount of at least one of the compounds defined afore to a human or an animal being in need thereof. All explanations on the compounds defined above, to which the present invention relates as such, for example on the groups in the compounds of the formula I, the physiologically acceptable salts, the preferred meanings or the preparation of the compounds, apply correspondingly to the compounds defined afore which can be used according to the invention.

The pharmaceutical compositions and medicaments according to the invention can be destined for enteral or parenteral use and normally comprise about 0.5 to about 90 percent by weight of the compounds of the formula I and/or their physiologically acceptable salts. The amount of active substance of the formula I and/or its physiologically acceptable salts in the pharmaceutical products and medicaments is generally about 0.2 to about 1000 mg, preferably about 0.2 to about 500 mg, particularly preferably about 1 to about 300 mg, per dosage unit. The pharmaceutical compositions and medicaments can be produced in a manner known per se. For this purpose, the compounds of the formula I and/or their physiologically acceptable salts are mixed together with one or more solid or liquid carrier substances and/or auxiliary substances, if desired also in combination with other active pharmaceutical ingredients, for example active pharmaceutical ingredients having cardiovascular activity, such as, for example, calcium antagonists, ACE inhibitors or β blockers, and are brought into a pharmaceutical form suitable for dosage and administration, which can then be used as pharmaceutical in human medicine or veterinary medicine.

Suitable carrier substances and auxiliary substances are organic and inorganic substances which are suitable, for example, for enteral administration, such as oral or rectal administration, or for parenteral administration, such as intravenous, intramuscular or subcutaneous injection or infusion, or for topical or percutaneous or transcutaneous administrations, and with which the compounds of the formula I or their physiologically acceptable salts do not react in an unwanted manner. Examples which may be mentioned are water, vegetable oils, waxes, alcohols such as ethanol, isopropanol, 1,2-propanediol, benzyl alcohols or glycerol, polyols, polyethylene glycols, polypropylene glycols, glycerol triacetate, gelatin, carbohydrates such as lactose or starch, stearic acid and its salts such as magnesium stearate, talc, lanolin, petrolatum, or mixtures thereof, for example mixtures of water with one or more organic solvents such as mixtures of water with alcohols. Pharmaceutical forms for oral and rectal use are in particular tablets, film-coated tablets, sugar-coated tablets, granules, hard and soft gelatin capsules, suppositories, solutions, preferably oily, alcoholic and aqueous solutions, syrups, elixirs and drops, and also suspensions or emulsions. Pharmaceutical forms for topical use are in particular ointments, creams, pastes, lotions, gels, sprays, foams, aerosols, solutions and powders. Further examples of suitable pharmaceutical forms are also implants and patches. The compounds of the formula I and their physiologically acceptable salts can also be lyophilized, and the resulting lyophilizates be used, for example, for producing pharmaceutical preparations for injection. In particular for topical use, also liposomal preparations are suitable. As examples of the types of auxiliary substances, or additives, which may be present in the pharmaceutical compositions and medicaments, lubricants, preservatives, thickeners, stabilizers, disintegrants, wetting agents, means for achieving a depot effect, emulsifiers, salts, for example for influencing the osmotic pressure, buffer substances, colorants, flavorings and aromatizing substances may be mentioned. The pharmaceutical compositions and medicaments may, if desired, also comprise one or more further pharmaceutical active substances and/or one or more vitamins, for example.

The compounds of the formula I and their physiologically acceptable salts and the pharmaceutical compositions and medicaments comprising them are used in particular as antiarrhythmics for the treatment of cardiac arrhythmias, or dysrhythmias, of a wide variety of origins and specifically for preventing sudden cardiac death, or sudden heart death, caused by arrhythmias. Examples of arrhythmic disorders of the heart are supraventricular arrhythmias such as, for example, atrial tachycardias, atrial flutter or paroxysomal supraventricular arrhythmias, or ventricular arrhythmias such as ventricular extrasystoles, and in particular life-threatening ventricular tachycardias or the particularly dangerous fatal ventricular fibrillation. They are particularly suitable for cases in which arrhythmias are the result of a constriction of a coronary vessel as occur, for example, in angina pectoris or during acute myocardial infarction or as chronic sequelae of a myocardial infarction. They are therefore particularly suitable for preventing sudden cardiac death in post-infarct patients. Further pathological states in which such arrhythmias and/or sudden cardiac death caused by arrhythmias are involved are, for example, cardiac insufficiency, or heart failure, and cardiac hypertrophy as a result of a chronically raised blood pressure.

In addition, the compounds of the formula I and their physiologically acceptable salts and the pharmaceutical compositions and medicaments comprising them are able to have a positive influence on a reduced contractility of the heart and a weakened force of myocardial contraction. This can be a decline, caused by chronic diseases, in the contractility of the heart as, for example, is associated with cardiac insufficiency, but also an acute case such as cardiac insufficiency associated with shock, for example septic shock, hemorrhagic shock or cardiac shock. The compounds according to the invention and their physiologically acceptable salts are particularly suitable for the treatment of the pathological changes in blood pressure occurring in association with septic shock. In general, the compounds according to the invention and their physiologically acceptable salts are suitable for improving cardiac function. Moreover, in the specific case of a heart transplant the heart can, after the operation has taken place, recover its functional capacity more quickly and more reliably under the influence of the compounds of the formula I and their physiologically acceptable salts. The same applies to operations on the heart requiring temporary cessation of cardiac activity through cardioplegic solutions.

The compounds of the formula I and their physiologically acceptable salts and the pharmaceutical compositions and medicaments comprising them can further be employed generally in the treatment of diseases which are associated with a dysfunction of the autonomic nervous system or a hypofunction or dysfunction of the vagal nervous system, especially on the heart, or which are caused by such dysfunction or hypofunction, or whose treatment aims at increasing or normalizing the activity of the vagal nervous system, for example a vagal dysfunction of the heart occurring as a result of a metabolic disorder such as, for example, diabetes mellitus. The compounds of the formula I and their physiologically acceptable salts and the pharmaceutical compositions and medicaments comprising them can also generally be employed for the treatment of diseases which are characterized by oxygen deficiency states, and of cerebrovascular disorders.

The dosage of the compounds of the formula I or of their physiologically acceptable salts depends, as usual, on the circumstances of the particular individual case and will be adapted by the skilled person according to the usual rules and procedures. It depends, for example, on the administered compound of the formula I, its potency and duration of action, on the nature and severity of the individual pathological state, on the gender, age, weight and individual response of the human or animal to be treated, on whether the treatment is acute or chronic or prophylactic, or on whether further active substances are administered in addition to the compound of the formula I. Normally, in the case of an administration to an adult weighing about 75 kg, a dose of about 0.1 mg to about 100 mg per kg and day, preferably about 1 mg to about 10 mg per kg and day (in each case in mg per kg of body weight) is sufficient. The daily dose can, for example, be administered in the form of a single oral or parenteral dose or divided into a plurality, for example two, three or four, single doses. Administration may also take place continuously. Parenteral administration, for example by injection or by continuous intravenous infusion, can be advantageous in particular when acute cases of cardiac arrhythmias are treated, for example in an intensive care unit. A preferred dose range in critical situations is then about 1 mg to about 100 mg per kg of body weight and day. Where appropriate, depending on the individual response, it may be necessary to deviate upward or downward from the indicated dosages.

Besides as pharmaceutical active substance in human medicine and veterinary medicine, the compounds of the formula I and their physiologically acceptable salts can also be employed, for example, as aid or scientific tool in biochemical investigations in which it is intended to influence ion channels, or for isolating or characterizing potassium channels. They can further be used for diagnostic purposes, for example in in vitro diagnoses of cell samples or tissue samples. The compounds of the formula I and their salts can also be used as chemical intermediates, for example for preparing further pharmaceutical actives substances.

The invention is explained by the following examples without being restricted thereto.

EXAMPLE 1

5-Chloro-2-methoxy-N-(2-(1-(3-methylthioureidosulfonyl)piperidin-4-yl)ethyl)benzamide

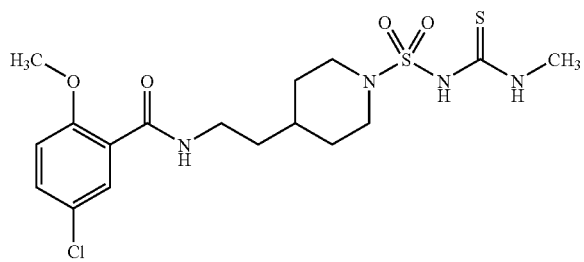 [SMILES: CNC(=S)NS(=O)(=O)N1CCC(CCNC(=O)c2cc(Cl)ccc2OC)CC1]

376 mg (1 mmol) of 4-(2-(5-chloro-2-methoxybenzamido)ethyl)piperidine-1-sulfonamide and 652 mg (2 mmol) of cesium carbonate were heated in 5 ml of N-methyl-2-pyrrolidone with 73 mg (1 mmol) of methyl isothiocyanate at 80° C. for 10 minutes. The reaction mixture was poured onto ice/2 M hydrochloric acid, and the precipitated solid was filtered off with suction and washed with water until neutral. Purification by chromatography (silica gel; toluene/ethanol/ethyl acetate 8/1/1) resulted in 90 mg (20%) of the title compound as a colorless solid.

M.p. (melting point): 151-153° C. (decomposition)
MS (ES+): 449.25 ((MS=mass spectrum; ES=electron spray ionization)
$^1$H-NMR (DMSO-$d_6$, 300 MHz): δ=11.10 (s, 1H), 8.40 (q, 1H), 8.20 (t, 1H), 7.60 (d, 1H), 7.50 (dd, 1H), 7.15 (d, 1H), 3.85 (s, 3H), 3.75 (d, 2H), 3.25 (m, 2H), 2.98 (d, 3H), 2.80 (dt, 2H), 1.80 (m, 2H), 1.42 (m, 3H), 1.15 (m, 2H)

EXAMPLE 2

5-Chloro-2-methoxy-N-(2-(1-(3-ethylthioureidosulfonyl)piperidin-4-yl)ethyl)benzamide

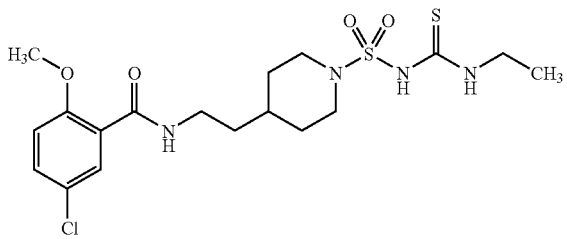

188 mg (0.5 mmol) of 4-(2-(5-chloro-2-methoxybenzamido)ethyl)piperidine-1-sulfonamide and 326 mg (1 mmol) of cesium carbonate were heated in 5 ml of N-methyl-2-pyrrolidone with 0.1 ml (1.1 mmol) of ethyl isothiocyanate at 80° C. for 10 minutes. The reaction mixture was poured onto ice/2 M hydrochloric acid and extracted three times with 10 ml of dichloromethane each time. The combined organic phases were washed with water until neutral, dried over sodium sulfate and filtered after addition of activated carbon. The crude product obtained after removal of the solvent was recrystallized from methanol/water. 80 mg (35%) of the title compound were obtained as a colorless solid.

M.p.: 138-140° C.
MS (ES+): 463.23
$^1$H-NMR (DMSO-$d_6$, 300 MHz): δ=11.00 (s, 1H), 8.40 (t, 1H), 8.20 (t, 1H), 7.60 (d, 1H), 7.50 (dd, 1H), 7.18 (d, 1H), 3.90 (s, 3H), 3.65 (d, 2H), 3.55 (m, 2H), 3.30 (m, 2H), 2.80 (dt, 2H), 1.80 (m, 2H), 1.45 (m, 3H), 1.15 (m, 2H), 1.10 (t, 3H)

EXAMPLE 3

5-Chloro-2-methoxy-N-(2-(1-(3-propylthioureidosulfonyl)piperidin-4-yl)ethyl)benzamide

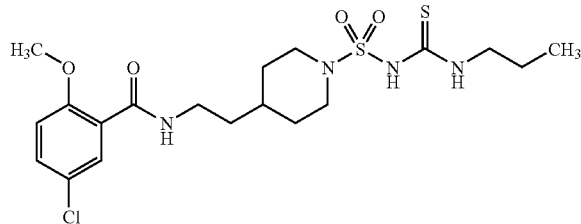 [SMILES: CCCNC(=S)NS(=O)(=O)N1CCC(CCNC(=O)c2cc(Cl)ccc2OC)CC1]

376 mg (1 mmol) of 4-(2-(5-chloro-2-methoxybenzamido)ethyl)piperidine-1-sulfonamide and 652 mg (2 mmol) of cesium carbonate were heated in 5 ml of N-methyl-2-pyrrolidone with 0.2 ml (1.8 mmol) of n-propyl isothiocyanate at 80° C. for 10 minutes. The reaction mixture was poured onto ice/2 M hydrochloric acid, and the precipitated solid was filtered off with suction and washed with water until neutral. The crude product obtained after purification by chromatography (silica gel; toluene/ethanol/ethyl acetate 8/1/1) was crystallized from ethyl acetate. 155 mg (33%) of the title compound were obtained as a colorless solid.

M.p.: 119-121° C.
MS (ES+): 477.15
$^1$H-NMR (DMSO-$d_6$, 300 MHz): δ=11.00 (s, 1H), 8.40 (t, 1H), 8.20 (t, 1H), 7.60 (d, 1H), 7.50 (dd, 1H), 7.18 (d, 1H), 3.90 (s, 3H), 3.65 (d, 2H), 3.45 (m, 2H), 3.25 (m, 2H), 2.80 (m, 2H), 1.80 (m, 2H), 1.58 (m, 2H), 1.45 (m, 3H), 1.08 (m, 2H), 0.85 (t, 3H)

EXAMPLE 4

5-Chloro-2-methoxy-N-(2-(1-(3-isopropylthioureidosulfonyl)piperidin-4-yl)ethyl)benzamide

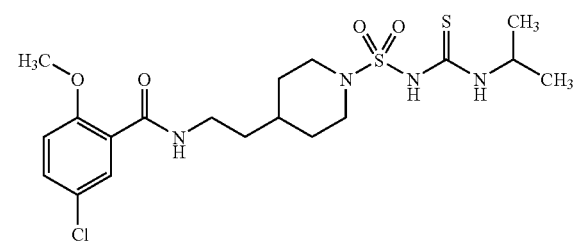

188 mg (0.5 mmol) of 4-(2-(5-chloro-2-methoxybenzamido)ethyl)piperidine-1-sulfonamide and 326 mg (1 mmol) of cesium carbonate were heated in 5 ml of N-methyl-2-pyrrolidone with 0.1 ml (0.9 mmol) of isopropyl isothiocyanate at 80° C. for 10 minutes. The reaction mixture was poured onto ice/2 M hydrochloric acid and extracted three times with 10 ml of dichloromethane each time. The combined organic phases were dried over sodium sulfate and filtered after addition of activated carbon. The crude product obtained after removal of the solvent was recrystallized from methanol. 142 mg (60%) of the title compound were obtained as a colorless solid.

M.p.: 145-147° C.

MS (ES+): 477.25

$^1$H-NMR (DMSO-$d_6$, 300 MHz): δ=11.00 (s, 1H), 8.20 (t, 1H), 8.10 (d, 1H), 7.60 (d, 1H), 7.50 (dd, 1H), 7.18 (d, 1H), 4.35 (m, 1H), 3.90 (s, 3H), 3.65 (d, 2H), 3.25 (m, 2H), 2.85 (m, 2H), 1.80 (m, 2H), 1.45 (m, 3H), 1.10 (m, 2H), 0.95 (d, 6H)

EXAMPLE 5

5-Chloro-2-methoxy-N-(2-(1-(3-cyclopropylthioureidosulfonyl)piperidin-4-yl)ethyl)benzamide

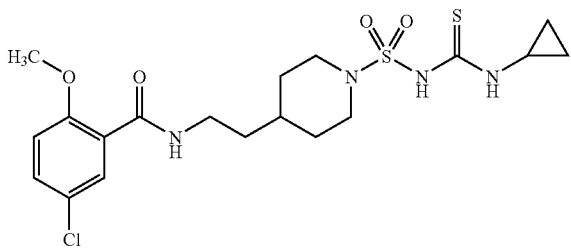 [SMILES: COc1ccc(Cl)cc1C(=O)NCCC1CCN(S(=O)(=O)NC(=S)NC2CC2)CC1]

376 mg (1 mmol) of 4-(2-(5-chloro-2-methoxybenzamido)ethyl)piperidine-1-sulfonamide and 652 mg (2 mmol) of cesium carbonate were heated in 5 ml of N-methyl-2-pyrrolidone with 0.2 ml (1.8 mmol) of cyclopropyl isothiocyanate at 80° C. for 10 minutes. The reaction mixture was poured onto ice/2 M hydrochloric acid, and the precipitated solid was filtered off with suction and washed with water until neutral. The crude product obtained after purification by chromatography (silica gel; toluene/ethanol/ethyl acetate 8/1/1) was crystallized from methanol/diethyl ether. 195 mg (41%) of the title compound were obtained as a colorless solid.

M.p.: 144-145° C.

MS (ES+): 475.41

$^1$H-NMR (DMSO-$d_6$, 400 MHz): δ=11.00 (s, 1H), 8.25 (m, 1H), 8.15 (m, 1H), 7.60 (d, 1H), 7.50 (d, 1H), 7.15 (d, 1H), 3.85 (s, 3H), 3.65 (d, 2H), 3.35 (m, 2H), 3.00 (m, 1H), 2.85 (m, 2H), 1.80 (m, 2H), 1.45 (m, 3H), 1.10 (m, 2H), 0.75 (m, 2H), 0.60 (m, 2H)

EXAMPLE 6

5-Chloro-2-methoxy-N-(2-(1-(3-cyclohexylthioureidosulfonyl)piperidin-4-yl)ethyl)benzamide

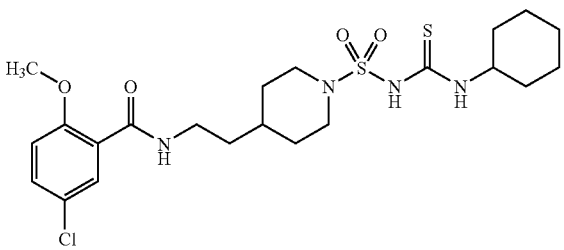 [SMILES: COc1ccc(Cl)cc1C(=O)NCCC1CCN(S(=O)(=O)NC(=S)NC2CCCCC2)CC1]

376 mg (1 mmol) of 4-(2-(5-chloro-2-methoxybenzamido)ethyl)piperidine-1-sulfonamide and 652 mg (2.0 mmol) of cesium carbonate were heated in 5 ml of N-methyl-2-pyrrolidone with 0.3 ml (2 mmol) of cyclohexyl isothiocyanate at 80° C. for 10 minutes. The reaction mixture was poured onto ice/2 M hydrochloric acid, and the precipitated solid was filtered off with suction, washed with water until neutral, dissolved in methanol, filtered after addition of activated carbon and crystallized using diethyl ether. 230 mg (45%) of the title compound were obtained as a colorless solid.

M.p.: 146-148° C.

MS (ES+): 517.18

$^1$H-NMR (DMSO-$d_6$, 400 MHz): δ=11.00 (s, 1H), 8.22 (t, 1H), 8.18 (d, 1H), 7.60 (d, 1H), 7.50 (d, 1H), 7.15 (d, 1H), 4.1 (m, 1H), 3.85 (s, 3H), 3.62 (d, 2H), 3.35 (m, 2H), 2.85 (m, 2H), 1.95-1.10 (m, 17H)

EXAMPLE 7

5-Chloro-2-methoxy-N-(2-(1-(3-methylureidosulfonyl)piperidin-4-yl)ethyl)benzamide

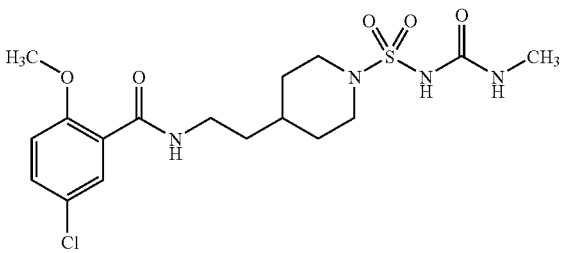

376 mg (1 mmol) of 4-(2-(5-chloro-2-methoxybenzamido)ethyl)piperidine-1-sulfonamide and 80 mg (2 mmol) of sodium hydroxide were heated in 5 ml of N-methyl-2-pyrrolidone with 180 mg (1 mmol) of N-methyltrichloroacetamide at 80° C. for 10 minutes. The reaction mixture was poured onto ice/2 M hydrochloric acid, and the precipitated solid was filtered off with suction and washed with water until neutral. Purification by chromatography (silica gel; toluene/ethanol/ethyl acetate 8/1/1) resulted in 25 mg (6%) of the title compound as a colorless solid.

M.p.: 134-136° C. (decomposition)
MS (ES+): 433.24
$^1$H-NMR (DMSO-$d_6$, 300 MHz): δ=10.00 (s, 1H), 8.20 (t, 1H), 7.60 (d, 1H), 7.50 (dd, 1H), 7.15 (d, 1H), 6.20 (q, 1H), 3.85 (s, 3H), 3.60 (d, 2H), 3.30 (m, 2H), 2.78 (dt, 2H), 2.60 (d, 3H), 1.80 (m, 2H), 1.45 (m, 3H), 1.15 (m, 2H)

EXAMPLE 8

5-Chloro-2-methoxy-N-(2-(1-(3-ethylureidosulfonyl)piperidin-4-yl)ethyl)benzamide

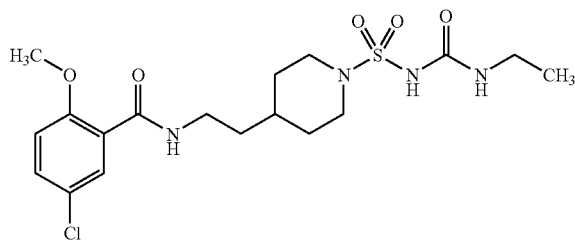 [SMILES: CCNC(=O)NS(=O)(=O)N1CCC(CCNC(=O)c2cc(Cl)ccc2OC)CC1]

0.1 ml (1.16 mmol) of 30% strength hydrogen peroxide solution was added to a solution of 46 mg (0.1 mmol) of 5-chloro-2-methoxy-N-(2-(1-(3-ethylthioureidosulfonyl)piperidin-4-yl)ethyl)benzamide in 2 ml of 0.5 M sodium hydroxide solution at 0° C. After the reaction mixture had been kept at 0° C. for 1.5 hours, 100 mg of sodium sulfite were added, and the mixture was acidified by means of 2 M hydrochloric acid. The precipitated solid was filtered off, washed with water until neutral and reprecipitated from diethyl ether/methanol. 19 mg (43%) of the title compound were obtained as a colorless solid.
M.p.: 121-130° C. (decomposition)
MS (ES+): 447.32

EXAMPLE 9

5-Chloro-2-methoxy-N-(2-(1-(3-propylureidosulfonyl)piperidin-4-yl)ethyl)benzamide

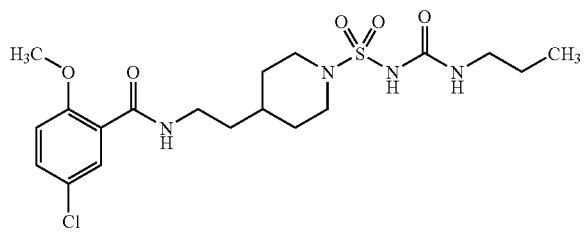

376 mg (1 mmol) of 4-(2-(5-chloro-2-methoxybenzamido)ethyl)piperidine-1-sulfonamide and 160 mg (4 mmol) of sodium hydroxide were heated in 5 ml of N-methyl-2-pyrrolidone with 410 mg (2 mmol) of N-(n-propyl)trichloroacetamide at 80° C. for 10 minutes. The reaction mixture was poured onto ice/2 M hydrochloric acid, and the precipitated solid was filtered off with suction and washed with water until neutral. Purification by chromatography (silica gel; toluene/ethanol/ethyl acetate 8/1/1) resulted in 65 mg (14%) of the title compound as a colorless solid.
M.p.: 140-142° C.

MS (ES+): 461.2
$^1$H-NMR (DMSO-$d_6$, 300 MHz): δ=9.80 (s, 1H), 8.20 (t, 1H), 7.60 (d, 1H), 7.55 (dd, 1H), 7.18 (d, 1H), 6.35 (t, 1H), 3.85 (s, 3H), 3.60 (d, 2H), 3.25 (m, 2H), 3.00 (q, 2H), 2.78 (m, 2H), 1.80 (m, 2H), 1.40 (m, 5H), 1.08 (m, 2H), 0.85 (t, 3H)

EXAMPLE 10

5-Chloro-2-methoxy-N-(2-(1-(3-isopropylureidosulfonyl)piperidin-4-yl)ethyl)benzamide 0.1 ml (1.16 mmol) of 30% strength hydrogen peroxide solution was added to a solution of 48 mg (0.1 mmol) of 5-chloro-2-methoxy-N-(2-(1-(3-isopropylthioureidosulfonyl)piperidin-4-yl)ethyl)benzamide in 2 ml of 0.5 M sodium hydroxide solution at 0° C. After the reaction mixture had been kept at 0° C. for 2 hours, 100 mg of sodium sulfite were added, and the mixture was acidified by means of 2 M hydrochloric acid. The precipitated solid was filtered off, washed with water until neutral and recrystallized from diethyl ether. 21 mg (45%) of the title compound were obtained as a colorless solid.
M.p.: 152-154° C.
MS (ES+): 447.32

EXAMPLE 11

5-Chloro-2-methoxy-N-(2-(1-(3-cyclopropylureidosulfonyl)piperidin-4-yl)ethyl)benzamide 0.2 ml (2.32 mmol) of 30% strength hydrogen peroxide solution was added to a solution of 96 mg (0.2 mmol) of 5-chloro-2-methoxy-N-(2-(1-(3-cyclopropylthioureidosulfonyl)piperidin-4-yl)ethyl)benzamide in 2 ml of 0.5 M sodium hydroxide solution at 0° C. After the reaction mixture had been kept at 0° C. for 1 hour, 200 mg of sodium sulfite were added, and the mixture was acidified by means of 2 M hydrochloric acid. The precipitated solid was filtered off, washed with water until neutral and purified by chromatography (silica gel; toluene/ethanol/ethyl acetate 8/1/1). The crude product was crystallized from methanol. 30 mg (32%) of the title compound were obtained as a colorless solid.
M.p.: 138-139° C.
MS (ES+): 459.44

¹H-NMR (DMSO-d$_6$, 400 MHz): δ=9.70 (s, 1H), 8.20 (m, 1H), 7.60 (d, 1H), 7.50 (d, 1H), 7.15 (d, 1H), 6.50 (m, 1H), 3.85 (s, 3H), 3.60 (d, 2H), 3.35 (m, 3H), 2.80 (m, 2H), 1.75 (m, 2H), 1.45 (m, 3H), 1.10 (m, 2H), 0.60 (m, 2H), 0.40 (m, 2H)

Pharmacological Investigations

1) Effect on the Action Potential Duration on the Guinea Pig Papillary Muscle

ATP deficiency states like those observed in the cardiomyocyte during an ischemia lead to a shortening of the action potential duration. They are regarded as one of the causes of so-called reentry arrhythmias, which can cause sudden cardiac death. The opening of ATP-sensitive potassium channels through the lowering of the ATP level is regarded as the cause thereof (ATP=adenosine triphosphate). For measuring the action potential on the guinea pig papillary muscle, a standard microelectrode technique was employed.

Guinea pigs of both sexes were sacrificed by a blow to the head, the heart was removed, and the papillary muscles were dissected out and suspended in an organ bath. The organ bath was rinsed with Ringer's solution (136 mmol/l NaCl, 3.3 mmol/l KCl, 2.5 mmol/l CaCl$_2$, 1.2 mmol/l KH$_2$PO$_4$, 1.1 mmol/l MgSO$_4$, 5.0 mmol/l glucose, 10.0 mmol/l 1-(2-hydroxyethyl)piperazine-4-(2-ethanesulfonic acid) (HEPES), pH adjusted to 7.4 with NaOH) and aerated with 100% oxygen at a temperature of 37° C. The muscle was stimulated via an electrode with square-wave pulses of 1 V and 1 ms duration and a frequency of 1 Hz. The action potential was derived through a glass microelectrode which is inserted intracellularly and filled with 3 mol/l KCl solution, and was recorded. The action potential was amplified using an amplifier from Hugo Sachs (March-Hugstetten, Germany) and stored and evaluated by a computer. The duration of the action potential was determined at a degree of repolarization of 90% (APD$_{90}$). The shortening of the action potential was induced after an equilibration time of 30 minutes by rinsing the papillary muscle with a hypoxic solution. For this, the glucose was removed, the HEPES buffer replaced by PIPES buffer (piperazine-1,4-bis(2-ethanesulfonic acid)), the pH adjusted to 6.5 and aeration was carried out with 100% nitrogen. This led after a period of 60 minutes to a marked shortening of the APD$_{90}$. After this time, the test substance was added in the form of a stock solution in propanediol, so that the concentration of the substance in the bath solution was 2 μmol/l. After a further 60 minutes, the re-prolongation of the action potential again recorded. The table below indicates the overall shortening, resulting after hypoxia and addition of test substance, of the APD$_{90}$ value in percent, i.e. the percentage shortening of the APD$_{90}$ still remaining after addition of the test substance under hypoxia, where 100% corresponds to the APD$_{90}$ value under hypoxic conditions before addition of the test substance and 0% corresponds to the APD$_{90}$ value under normoxic conditions at the start of the experiment.

| Substance | Remaining shortening of the APD$_{90}$ under hypoxia in percent |
|---|---|
| Example 1 | 80% |
| Example 2 | 82% |
| Example 3 | 67% |
| Example 4 | 54% |
| Example 7 | 68% |
| Example 8 | 54% |

The values obtained demonstrate the normalizing effect of the compounds according to the invention on a hypoxically shortened action potential duration.

2) Effect on hSUR1/hKir6.2-Transfected CHO Cells (Hypoglycemic Effect)

The mechanism of action of blood sugar-lowering sulfonylureas such as, for example, of glibenclamide has been roughly elucidated. The target organ of these compounds is the β cell of the pancreas, where they block ATP-sensitive potassium channels and bring about, through influencing the electric potential of the cell membrane, a release of the blood sugar-lowering hormone insulin. In molecular biology terms, pancreatic ATP-sensitive potassium channels are composed of the sulfonylurea receptor SUR1 and of the inwardly rectifying potassium channel Kir6.2 (Inagaki et al., Science 270, 1166-1170 (1995); Inagaki et al., Neuron 16, 1011-1017 (1996)). A hypoglycemic compound such as, for example, glibenclamide brings about, through binding to the sulfonylurea receptor, a depolarization of the cell membrane leading to increased influx of calcium ions and, as a consequences thereof, a release of insulin. The extent of this depolarization of the cell membrane caused by the compounds according to the invention was investigated on CHO cells which were transfected with the cloned components of human pancreatic ATP-sensitive potassium channels, hSUR1 and hKir6.2, and were activated by pretreatment with diaxozide, an opener of ATP-sensitive potassium channels. The strength of action of a compound on the membrane potential of these transfected and activated CHO cells is a measure of the blood sugar-lowering potential of this compound.

The CHO cells, which showed stable expression of human SUR1 and Kir6.2, were seeded in 96-well microtiter plates on the day before the measurement. On the day of the measurement, the microtiter plates were washed three times with PBS (physiological buffer solution). 90 μl remained in each well at the last washing step. The cells were then loaded with the fluorescent dye DiBAC$_4$ (Molecular Probes, Portland, Oreg., USA) by adding 90 μl of a 10 micromolar solution of DIBAC$_4$ in PBS and 90 μl of a 400-micromolar solution of diaxozide in PBS to each well. After an incubation time of 30 minutes at 37° C., the microtiter plates were then transferred into a Fluorescent Microtiter Plate Reader (FLIPR; Molecular Devices, Sunnyvale, Calif., USA). The cells were excited using an argon laser (Innova 90; Coherent, Santa Clara, Calif., USA) at a wavelength of 488 nm, and the fluorescence emission was measured using a CCD camera. Measurement of the membrane potential began after 4 minutes by adding 20 μl of a solution of the test substance or of the control solution to each well, measuring the resulting fluorescence emission every 20 seconds over a period of 20 minutes. The data listed below are averages of at least 4 experiments.

The following results were obtained.

| Substance | hSUR1/hKir6.2 blockade at 0.1 μM | hSUR1/hKir6.2 blockade at 1 μM | hSUR1/hKir6.2 blockade at 10 μM |
|---|---|---|---|
| Example 1 | <1% | 2% | 41% |
| Example 2 | <1% | 4% | 67% |
| Example 3 | 5% | 55% | 89% |
| Example 4 | 2% | 53% | 89% |
| Example 7 | <1% | 15% | 60% |
| Example 8 | 8% | 55% | 102% |
| Comparison (1) | 93% at 0.01 μM | | |

(1) For comparison, the effect of glibenclamide as an example of a substance having a hypoglycemic effect was determined.

The values obtained demonstrate that the inventive compounds have no or only a slight blood sugar-lowering effect.

3) Effect on Coronary Flow Under Hypoxic Conditions in the Guinea Pig Heart

It is known that an oxygen deficiency in coronary vessels leads to a reflectory dilatation of the vessels in order to compensate the oxygen deficiency. The vascular KATP channel (SUR2B/Kir6.2) plays an important part in this. Its opening leads to hyperpolarization of the cell membrane of the smooth muscle cell and consequently to a reduced calcium influx, resulting in a dilatation of the vessel. Blockade of the vascular KATP channel inhibits the widening of the vessel and thus adjustment of the coronary flow under hypoxic conditions. The test model used for determining the coronary flow was an isolated perfused Langendorff heart of a guinea pig.

Guinea pigs of both sexes were sacrificed by a blow to the head. The heart was quickly removed, and the aorta was canulated. After the canulation, the heart was suspended in the perfusion solution in the Langendorff apparatus, and a latex balloon was inserted into the left ventricle. The coronary flow was recorded using a flow transducer, type E, from Hellige (Freiburg, Germany). The heart was perfused with a constant pressure of 55 mm Hg. Hypoxia was induced by changing the aeration from 95% oxygen/5% carbon dioxide (=normoxia) to 20% oxygen/75% nitrogen/5% carbon dioxide. The coronary flow in the control, i.e. without addition of a test substance to the perfusate, was 7.9 ml/minute at normoxia and rose to 15.0 ml/minute under hypoxic conditions. The test substance was added to the perfusate 10 minutes before starting the hypoxia and was present in the indicated concentration. Below, the coronary flow under hypoxic conditions in percent of the coronary flow of the control under hypoxic conditions is indicated. The indicated values are averages of measurements on 3 hearts.

| Substance | Concentration | Hypoxic coronary flow compared with the control in percent |
|---|---|---|
| Example 4 | 1 µM | 61% |
| Comparison (1) | 1 µM | 35% |

(1) For comparison, the effect of glibenclamide as an example of a substance having a strong effect on the vascular KATP channel was determined.

The values obtained demonstrate that the compounds according to the invention have only a slight effect on the vascular KATP channel.

The invention claimed is:

1. A compound of formula I,

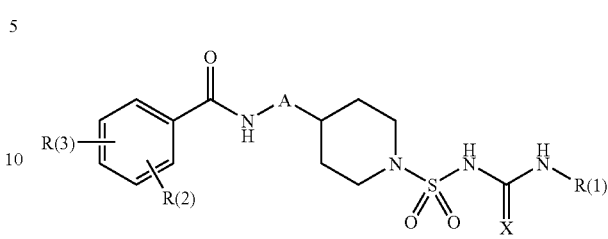

in which
A is $CH_2$, $CH_2$—$CH_2$ or $CH_2$—$CH_2$—$CH_2$;
X is sulfur;
R(1) is selected from hydrogen, $(C_1$-$C_3)$-alkyl, and cyclopropyl groups, wherein said $(C_1$-$C_3)$-alkyl and cyclopropyl groups may be substituted one or more times by fluorine; and
R(2) and R(3) are independently selected from hydrogen, halogen, $(C_1$-$C_4)$-alkyl, and $(C_1$-$C_4)$-alkoxy, wherein the $(C_1$-$C_4)$-alkyl and $(C_1$-$C_4)$-alkoxy groups can be substituted one or more times by fluorine;
in all its stereoisomeric forms and mixtures thereof in all ratios, and its physiologically acceptable salts.

2. The compound of formula I as claimed in claim 1, in which A is $CH_2$—$CH_2$, in all its stereoisomeric forms and mixtures thereof in all ratios, and its physiologically acceptable salts.

3. The compound of formula I as claimed in claim 1, in which the phenyl group carrying the groups R(2) and R(3) is a 2-$(C_1$-$C_4)$-alkoxy-5-halophenyl group, in all its stereoisomeric forms and mixtures thereof in all ratios, and its physiologically acceptable salts.

4. A pharmaceutical composition which comprises one or more compounds of formula I as claimed in claim 1 or their physiologically acceptable salts and a pharmaceutically acceptable carrier.

5. The compound of claim 1, wherein R(1) is selected from hydrogen and $(C_1$-$C_3)$-alkyl groups.

6. The compound of claim 1, wherein R(1) is selected from hydrogen and $(C_1$-$C_2)$-alkyl groups.

7. The compound of claim 1, wherein R(1) is selected from $(C_1$-$C_2)$-alkyl groups.

* * * * *